United States Patent [19]

Burns

[11] Patent Number: 5,035,705
[45] Date of Patent: Jul. 30, 1991

[54] METHOD OF PURGING A BALLOON CATHETER

[75] Inventor: Matthew M. Burns, Minneapolis, Minn.

[73] Assignee: SciMed Life Systems, Inc., Maple Grove, Minn.

[21] Appl. No.: 376,619

[22] Filed: Jul. 7, 1989

Related U.S. Application Data

[63] Continuation-in-part of Ser. No. 297,078, Jan. 13, 1989, abandoned.

[51] Int. Cl.$^5$ ............................................. A61M 29/02
[52] U.S. Cl. ...................................... 606/194; 604/99
[58] Field of Search ..................... 128/657, 658, 772; 604/52, 53, 96–103, 164, 167, 247, 256; 606/191–194, 196

[56] References Cited

U.S. PATENT DOCUMENTS

| | | | |
|---|---|---|---|
| 3,402,717 | 9/1968 | Doherty | 604/99 X |
| 3,675,658 | 7/1972 | Taylor . | |
| 3,707,151 | 12/1972 | Jackson | 604/96 X |
| 3,726,283 | 4/1973 | Dye et al. | 604/99 |
| 4,102,342 | 7/1978 | Akiyama et al. . | |
| 4,240,411 | 12/1980 | Hosono | 604/167 X |
| 4,285,341 | 8/1981 | Pollack . | |
| 4,292,974 | 10/1981 | Fogarty et al. | 606/194 |
| 4,323,071 | 4/1982 | Simpson et al. | 128/343 |
| 4,413,989 | 11/1983 | Schjeldahl et al. | 604/96 |
| 4,545,367 | 10/1985 | Tucci . | |
| 4,606,347 | 8/1986 | Fogarty et al. | 128/344 |
| 4,638,805 | 1/1987 | Powell | 128/344 |
| 4,646,742 | 3/1987 | Packard et al. | 606/194 |
| 4,665,925 | 5/1987 | Millar | 604/96 X |
| 4,684,363 | 8/1987 | Ari et al. | 604/98 |
| 4,715,378 | 12/1987 | Pope, Jr. et al. | 128/344 |
| 4,762,129 | 8/1988 | Bonzel . | |
| 4,793,350 | 12/1988 | Mar et al. . | |
| 4,813,934 | 3/1989 | Engelson et al. | 604/99 |
| 4,813,938 | 3/1989 | Raulerson | 604/167 |
| 4,819,637 | 4/1989 | Dormandy, Jr. et al. . | |
| 4,848,344 | 7/1989 | Sos et al. | 604/96 |
| 4,932,959 | 6/1990 | Horzewski et al. | 606/194 |

Primary Examiner—John D. Yasko
Assistant Examiner—Adam J. Cermak
Attorney, Agent, or Firm—Kinney & Lange

[57] ABSTRACT

A method for purging a dilatation catheter begins with providing an inflatable balloon at a distal end of a hollow shaft which has a longitudinal lumen defined therein, an inlet in communication with the interior of the balloon and extending to a lumen outlet distally of the inlet. To purge the catheter of gas before use, the lumen is filled with liquid from a proximal end of the shaft until liquid is forced out of the lumen through the lumen outlet. A guide wire is then advanced distally through the lumen, and a liquid-tight seal is formed about the guide wire distally of the inlet. With the seal maintained, the liquid is then withdrawn from the balloon, thereby deflating the balloon for introduction into a patient and ultimately, for reinflation and dilatation.

8 Claims, 4 Drawing Sheets

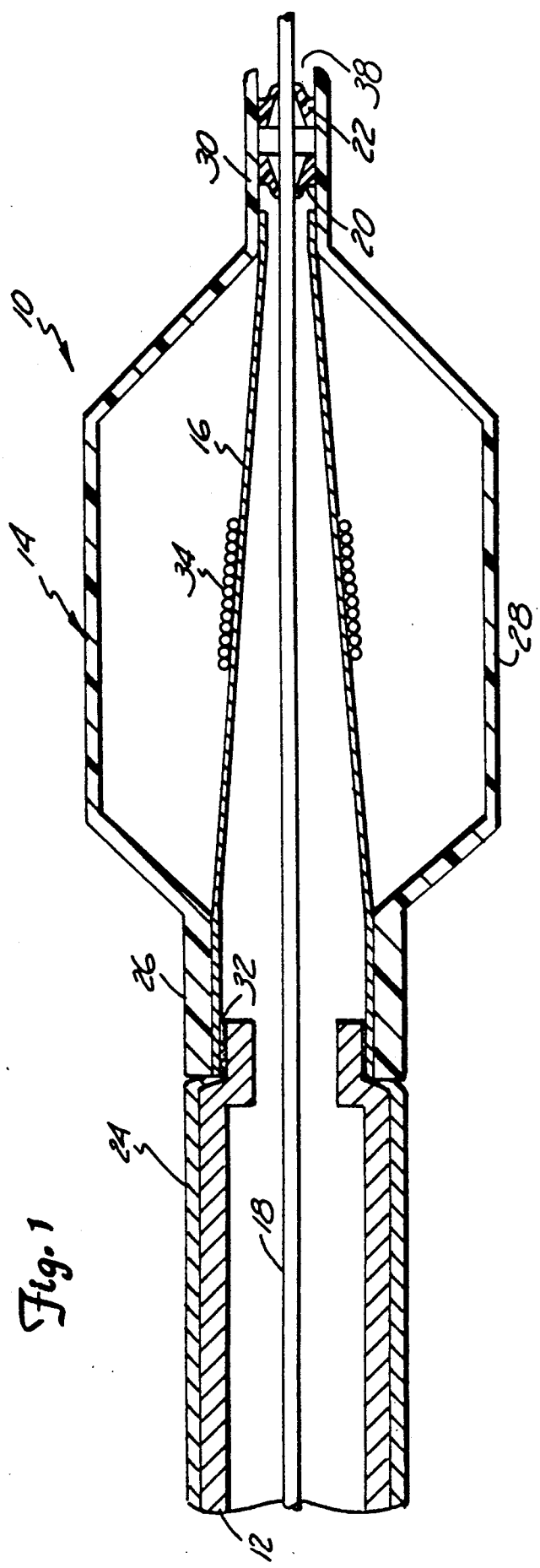

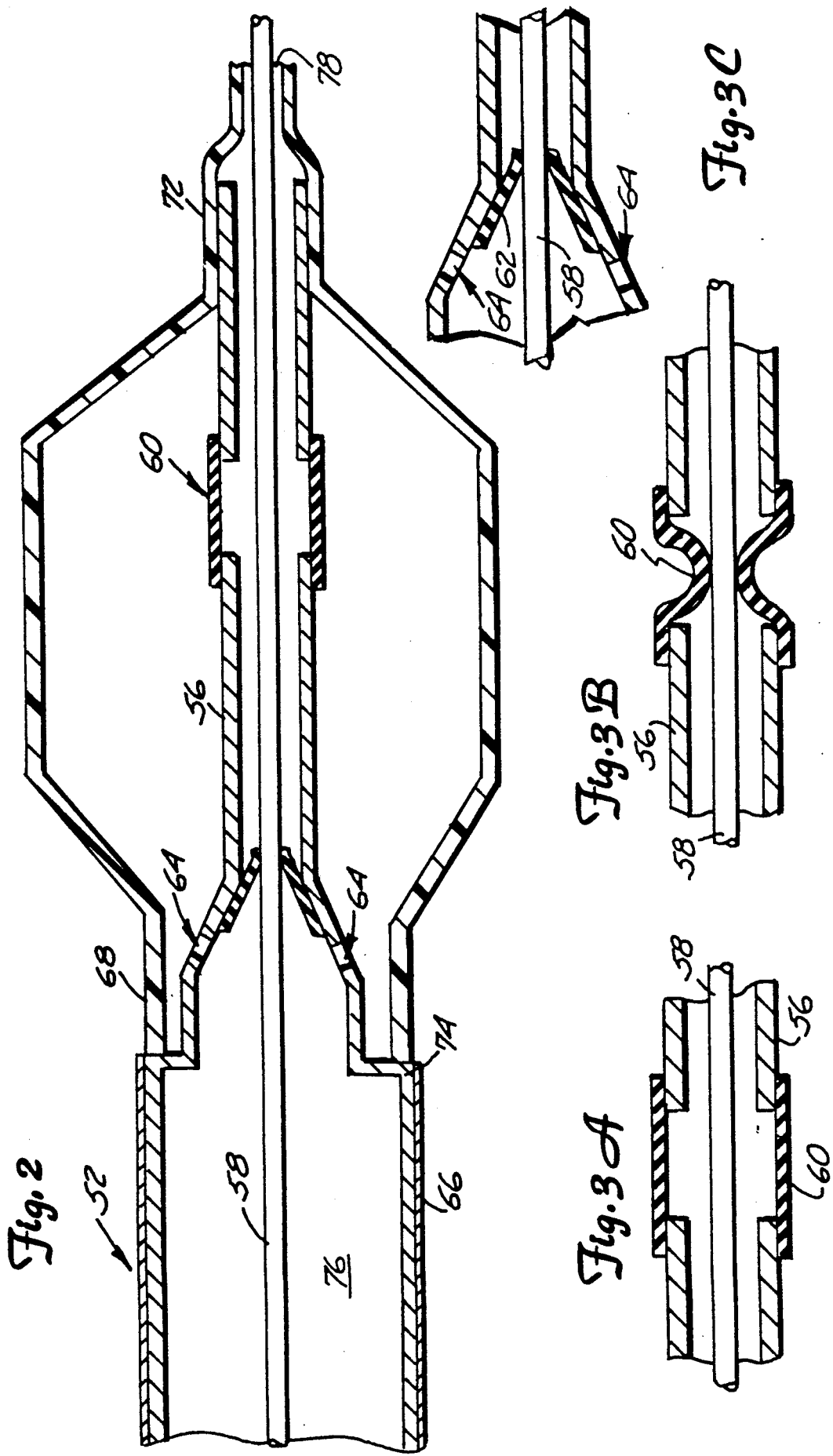

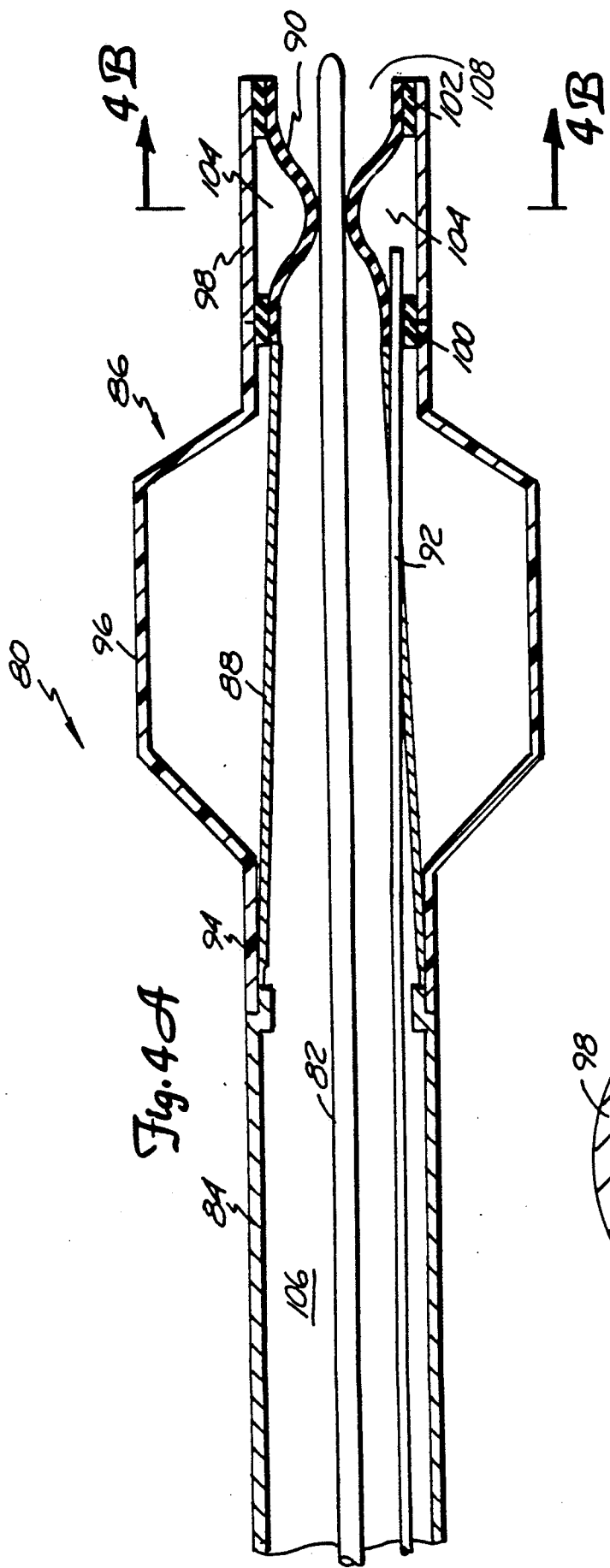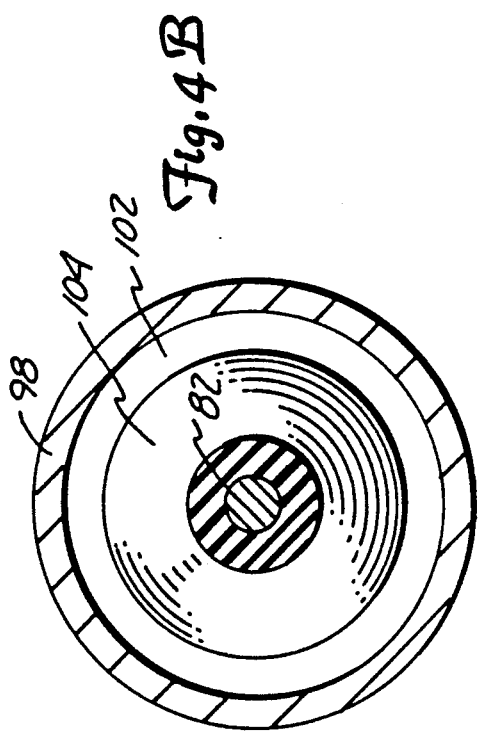

METHOD OF PURGING A BALLOON CATHETER

This application is a continuation-in-part application from U.S. patent application Ser. No. 07/297,078, filed Jan. 13, 1989, now abandoned.

BACKGROUND OF THE INVENTION

1. Field of the Invention

The present invention relates to the field of angioplasty. In particular, the present invention relates to a method of purging a dilatation balloon catheter.

2. Description of the Prior Art

Angioplasty has gained wide acceptance in recent years as an efficient and effective method for treating types of vascular diseases. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying fluid pressure through an inflation lumen to the balloon. The inflation of the balloon causes stretching of the artery and pressing of the lesion into the artery wall to reestablish acceptable blood flow through the artery.

Before a dilatation catheter is used in an angioplasty procedure, the balloon and catheter must be purged of any air to prevent the possibility of air entering the vascular system. The purging of air from the balloon and catheter with radiopaque purging/inflation fluid also presents the advantage of making the catheter more visible under fluoroscopy. Typically, purging of the catheter can be accomplished either by a distal venting device, as in U.S. Pat. No. 4,638,805, or via the provision of two separate lumens to the balloon. In the latter case, one lumen is used to introduce liquid into the catheter and balloon and the second lumen is provided to allow the purged air to escape, as in U.S. Pat. No. 4,323,071. The purging lumen may be permanently incorporated into the catheter or may be removable after purging. A disadvantage of these purging methods is the requirement of two separate lumens.

In order to treat very tight stenoses with small openings, there has been a continuing effort to reduce the profile (and shaft diameter) of the catheter so that the catheter cannot only reach but also cross very tight stenoses. A successful dilatation catheter must also be sufficiently flexible to pass through tight curvatures through the very tortuous path of the vascular system. A further requirement of a successful dilatation catheter is its "pushability".

This involves the transmission of longitudinal force along the catheter from its proximal end to its distal end so that a physician can push the catheter through the vascular system and the stenosis.

Two types of dilatation catheters are "over-the-wire" catheters and "non-over-the-wire" catheters. An over-the-wire catheter is one in which a separate guide wire lumen is provided so that a guide wire can be used to establish the path to the stenosis. The dilatation catheter can then be fed over the guide wire until the balloon is positioned within the stenosis. One problem with the over-the-wire catheter is the requirement of a larger profile (and shaft) in order to allow for the separate guide wire lumen.

A non-over-the-wire catheter acts as its own guide wire, and thus there is no need for a separate guide wire lumen. One advantage of a non-over-the-wire catheter is its potential for reduced profile (and shaft) since a guide wire lumen is not required. However, one disadvantage is the inability to maintain the position of the guide wire within the vascular system when removing the catheter and replacing it with one of a smaller (or larger) balloon diameter. Thus, with the non-over-the-wire catheter, the path to the stenosis must be reestablished when replacing the catheter with one having a different balloon diameter.

SUMMARY OF THE INVENTION

The catheter purging method of the present invention does not require separate lumens nor a distal venting device to purge a catheter and balloon of air. The inventive method is for use in connection with an inflatable balloon at the distal end of a shaft which has a lumen extending therethrough. The lumen has at least one inlet in communication with an interior of the balloon and extends to a lumen outlet distally of the inlet. The lumen is filled with liquid from a proximal end of the shaft so that liquid is forced out of the lumen through the lumen outlet. A guide wire is then advanced distally through the lumen and a liquid-tight seal is formed about the guide wire distally of the inlet.

The shaft lumen is thus purged of unwanted air, and then by advancing the guide wire, a seal is formed about the guide wire. Preferably, the balloon is provided in an initially uninflated state, wrapped spirally about itself to define a low profile in lateral cross-section. When the lumen outlet is sealed, via the advancement of the guide wire, the balloon can be filled with liquid to place the balloon in a fully inflated state wherein the balloon is unwrapped. The physician can then check the balloon for leaks and otherwise determine whether it is ready for use. The inflation medium can then be withdrawn proximally from the balloon, returning the balloon to its initial spirally-wrapped, uninflated state.

The inventive method can be undertaken with or without a guide wire placed in the lumen proximal to the lumen outlet. In a preferred embodiment of the inventive method, the distal end of a guide wire is positioned just proximal to the lumen outlet prior to filling the lumen with inflation medium. This thus provides the physician with a very quick and simple method for purging the catheter and balloon of unwanted gases prior to use.

The catheter of the present invention is an over-the-wire catheter which does not require separate inflation and guide wire lumens. The catheter includes a main shaft, an inflatable balloon enclosing a guide wire director, and a means for providing a fluid tight seal around the guide wire. The shaft is an elongate hollow thin wall tube having a proximal end and a distal end, and having a lumen extending therethrough from the proximal end to the distal end. A first end of the inflatable balloon is connected to the distal end of the shaft and a proximal end of the guide wire director. A second end of the inflatable balloon is connected to a distal end of the guide wire director. The interior of the balloon is in fluid communication with the lumen of the shaft. The means for providing a fluid tight seal around the guide wire is positioned in the distal portion of the catheter to allow for inflation and deflation of the balloon.

In one preferred embodiment of the present invention, the guide wire director comprises a permeable material acting as a port communicating an inflation medium between the lumen and the balloon interior. The means for providing a fluid tight seal in order to inflate and deflate the balloon comprises inflation and deflation valves positioned in or near the distal end of the balloon which close on the guide wire during inflation and deflation of the balloon so as not to permit fluid leakage into/out of the second end of the balloon while inflating/deflating.

In another preferred embodiment of the present invention, the guide wire director is integral with and of similar construction to the main shaft, but has a smaller diameter. The guide wire director contains perforations which act as ports communicating an inflation medium between the lumen and the balloon interior. The means for providing a fluid tight seal comprises inflation and deflation valves positioned within the interior of the balloon which collapse onto the guide wire during application of positive or negative fluid pressure.

In still another embodiment, an inflatable/deflatable valve located in the balloon acts as the means for providing a fluid tight seal. The valve is controlled by fluid pressure/vacuum supplied through a small diameter tube extending through the interior of the shaft and the guide wire director.

BRIEF DESCRIPTION OF THE DRAWINGS

FIG. 1 is a sectional view of a first preferred embodiment of the balloon catheter of the present invention, showing the balloon in an inflated state.

FIG. 2 is a sectional view of a second preferred embodiment of the balloon catheter of the present invention.

FIG. 3A is a detail view of the inflation valve shown in FIG. 2 under zero fluid pressure.

FIG. 3B is a detail view of the inflation valve shown in FIG. 2 collapsed upon the guide wire under 1 atm pressure within the balloon.

FIG. 3C is a detail view showing collapse of the deflation valve on wire during application of a vacuum to the interior of the shaft.

FIG. 4A and 4B are sectional views of a third preferred embodiment of the balloon catheter of the present invention.

DETAILED DESCRIPTION OF THE PREFERRED EMBODIMENTS

Figure 5:
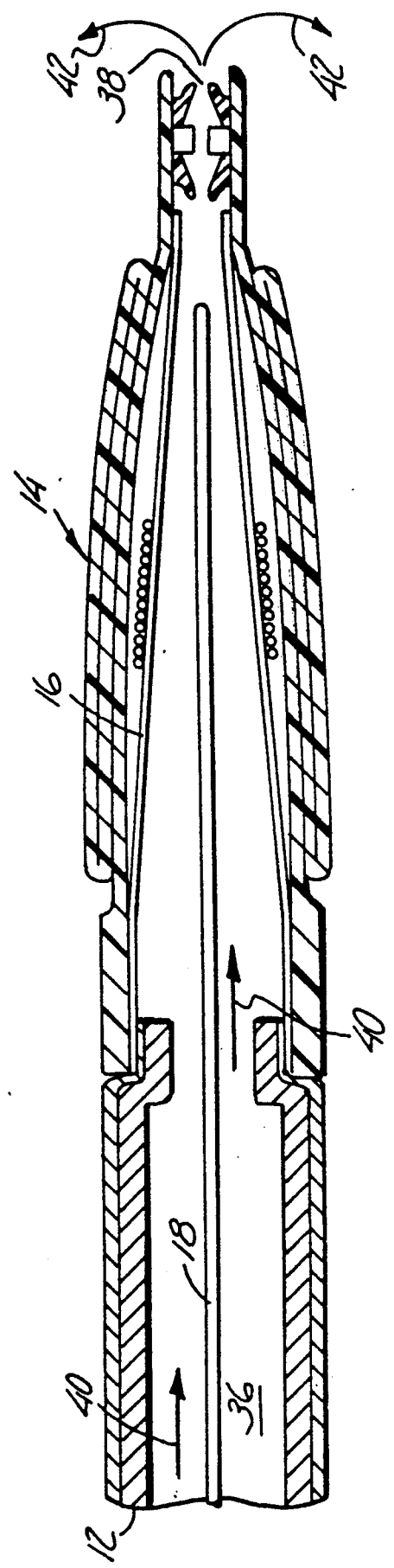
FIG. 5 is a sectional view of the first preferred embodiment of the present invention, showing the balloon catheter of FIG. 1 in an uninflated state, with the guide wire not yet moved distally across the inflation/deflation valve.

A catheter 10 shown in FIG. 1 is a dilatation balloon catheter, for use with guide wire 18, which includes catheter shaft 12, balloon member 14, guide wire director 16, inflation valve 20 and deflation valve 22.

Shaft 12 is an elongated flexible tube, preferably of stainless steel or polyimide with a low friction coating 24 such as Paralene or Teflon. Depending on the characteristics desired, shaft 12 can be of an integral or multipart construction. In the embodiment shown in FIG. 1, shaft 12 has an inside diameter of about 0.027 inch, an outside diameter of about 0.031 inch, and a shaft coating 24 thickness of about 0.0008 inch. Shaft 12 is mounted at its proximal end to an inflation device (not shown) which provides fluid under pressure to the lumen of shaft 12 for balloon inflation.

Balloon member 14, which is preferably a polymer material such as polyolefin, has a proximal or waist segment 26, a distensible balloon segment 28, and a small diameter distal segment 30. Proximal segment 26 is bonded to the distal end of shaft 12 and to the proximal end of guide wire director 16. Bonding material 32 is provided to seal together shaft 12 and guide wire director 16 with proximal segment 26 of balloon member 14.

In the embodiment shown in FIG. 1, guide wire director 16 extends through the interior of balloon member 14 with its diameter decreasing uniformly therethrough. The proximal end of guide wire director 16 is bonded by bonding material 32 (such as by an epoxy) to the distal end of shaft 12, and the distal end of guide wire director 16 is bonded to the distal segment 30 of balloon member 14. Guide wire director 16 is comprised of a permeable plastic material such that it acts as a port communicating an inflation medium between shaft 12 and balloon member 14. A radiopaque spring 34 surrounds guide wire director 16 at the central location of distensible balloon segment 28. Radiopaque spring 34 acts as a marker before the inflation medium is injected into and inflates distensible balloon segment 28. Thus, the physician can determine when balloon member 14 is properly positioned across the stenosis.

In FIG. 1, distal segment 30 of balloon member 14 contains inflation valve 20 and deflation valve 22 bonded therein. Guide wire 18 extends through shaft 1 and through balloon member 14. The inflation/deflation valve system permits guide wire 18 to pass through distal segment 30 of balloon member 14, but closes upon guide wire 18 during inflation and deflation of distensible balloon segment 28. Upon inflation, the inflation medium will pass through permeable plastic guide wire director 16 to inflate distensible balloon segment 28. Inflation valve 20 will simultaneously close on guide wire 18 thus providing a fluid tight seal. Upon deflation, the inflation medium will evacuate distensible balloon segment 28 by passing back through permeable plastic guide wire director 16. Deflation valve 22 will simultaneously close on guide wire 18 again providing a fluid tight seal. The inflation/deflation valve system of the present invention prevents any inflation medium from entering the vascular system during inflation, and prevents any blood or other body fluid from entering balloon catheter 10 during deflation.

A significant advantage of the present invention is the possibility for a very low profile catheter. Shaft 12 of catheter 10 acts as an inflation lumen as well as a guide wire path. Thus, a separate guide wire lumen is not required. The removal of the inner guide wire lumen (such as in a coaxial over-the-wire catheter) allows for a significantly smaller shaft 12.

FIG. 2 shows dilatation catheter 50, which is another embodiment of the present invention. Catheter 50, which is used in conjunction with guide wire 58, includes catheter shaft 52, balloon member 54, guide wire director 56, and valves 60 and 62.

Shaft 52 is an elongated flexible thin wall tube, preferably made of stainless steel or polyimide, with a low friction coating 66 such as Paralene or Teflon. Again, shaft 52 can be of an integral or multipart construction. Shaft 52 is mounted at its proximal end to an inflation device (not shown) which provides fluid under pressure to the lumen of shaft 52 for balloon inflation/vacuum deflation.

Balloon member 54, which is preferably a polymer material, has a proximal or waist segment 68, a distensible balloon segment 70, and a small diameter distal segment 72. Proximal segment 68 is bonded to the distal end of shaft 52 and to the proximal end of guide wire director 56.

In the embodiment shown in FIG. 2, guide wire director 56 extends through the interior of balloon member 54 with its diameter increasing near proximal segment 68. Guide wire director 56 is integral with and the same entity as shaft 52, and is thus a non-porous material. The distal end of guide wire director 56 is bonded to distal segment 72 of balloon member 54. Perforations 64 in guide wire director 56 act as a port communicating an inflation medium between shaft 52 and the interior of balloon member 54.

In FIG. 2, inflation valve 60 and deflation valve 62 are shown. Inflation valve 60 and deflation valve 62 are preferably made of flexible polymeric material. Guide wire 58 extends through shaft 52, through balloon member 54, and out of and beyond distal segment 72 of balloon member 54 and the distal end of guide wire director 56. Upon inflation, an inflation medium passes through perforations 64 to inflate distensible segment 70 of balloon member 54. Inflation valve 60 simultaneously closes on guide wire 58, thus providing a fluid tight seal between inflation valve 60 and guide wire 58. FIG. 3A shows inflation valve 60 in FIG. 2 under zero inflation medium pressure. FIG. 3B shows inflation valve 60 collapsed upon guide wire 58 during inflation under 1 atm inflation medium pressure. Upon deflation, the inflation medium evacuates distensible balloon segment 70 by passing back through perforations 64 of non-porous guide wire director 56. As shown in FIG. 3C, deflation valve 62 simultaneously closes on guide wire 58, providing a fluid tight seal between valve 62 and guide wire 58.

FIGS. 4A and 4B show dilatation catheter 80, which is still another embodiment of the present invention. Catheter 80 is used in conjunction with guide wire 82. Catheter 80 includes shaft 84, balloon member 86, guide wire director 88, bladder valve 90, and bladder inflation/deflation tube 92. Catheter 80 is an over-the-wire type of dilatation balloon catheter which is moveable with respect to guide wire 82.

Shaft 84 is an elongated, flexible tube which may be of a single or multipart construction. In one preferred embodiment, shaft 84 is a stainless steel or polyimide material, with a low friction coating.

Balloon member 86, which is preferably a polymer material, has a proximal or waist portion 94, a distensible balloon segment 96, and a distal segment 98. Proximal segment 94 of balloon member 86 is bonded or otherwise attached to the distal end of shaft 84.

Guide wire director 88 extends through the interior of balloon member 86. Guide wire director 88 is permeable, to allow fluid communication between the lumen of shaft 84 and the interior of distensible segment 96 of balloon member 86. The proximal end of guide wire director 88 is bonded or otherwise attached to the distal end of shaft 84, the proximal segment 94 of balloon member 86, or both.

At its distal end, guide wire director 88 is attached to bladder valve 90 within the interior of distal segment 98. The distal end of guide wire director 88, and the proximal end of bladder valve 90 are attached by a ring 100 of a bonding material (such as epoxy) to the interior of distal segment 98. A second ring 102 of bonding material attaches the distal end of bladder valve 90 to the interior of distal segment 98 of balloon member 86.

Tube 92 extends from the proximal end of catheter 80 through shaft 84 and the interior of balloon member 86 into cavity 104, which is an annular cavity defined by bladder valve 90, distal segment 98, and rings 100 and 102 of bonding material. Bladder valve 90 can be inflated so as to surround and form a fluid-type seal around guide wire 82 by applying fluid under pressure through tube 92 to cavity 104. Bladder 90 is inflated by a low viscosity fluid to act as a shut off valve during inflation and deflation of balloon segment 96. In this embodiment, the lumen of shaft 84 and the inner lumen of tube 92 are attached to separate manifolds (not shown) at the proximal end of catheter 80.

As mentioned, the shaft can be of multipart construction. For example, in a typical catheter shaft of approximately 54 inches, the first 42 inches from the proximal end of the shaft are "hypotube" (stainless steel hypodermic needle tube), while the last 12 inches are a flexible polymer tube (e.g., HDPE). In this case, the distal end of the hypotube and proximal end of the flexible polymer tube are bonded together, and the distal end of the flexible polymer tube and proximal end of the balloon member are bonded together (or the flexible polymer tube and balloon member may be integral). Indeed, in one embodiment, the shaft and balloon member are integrally formed from a suitable polymer material.

The catheter improvements described above permit the use of a unique gas purging procedure to prepare a dilatation catheter for use. The inflation-deflation valve allows gas to be vented from the distal end of the catheter and the balloon to be inflated and deflated by the physician before its introduction into the patient's body. The inventive process for purging is performed much more efficiently and quickly, factors which of course are critical and valuable in an angioplasty procedure.

The inventive method of purging a catheter is illustrated in connection with the catheter 10 shown in FIG. 1, and also in FIG. 5, and proceeds as follows. Inflatable balloon 14 is initially in an uninflated state, wrapped spirally about itself, as shown in FIG. 5. A shaft lumen 36 of catheter 10 is filled with inflation medium (typically a saline solution) from a proximal end of shaft 12 until inflation medium is forced out of lumen 36 through a distal lumen outlet 38. The distal flow of inflation medium is demonstrated by arrows 40 in FIG. 5. The expulsion of inflation medium out of lumen outlet 38 is demonstrated by arrows 42 in FIG. 5.

The inflation medium is delivered from the proximal end of shaft 12 through lumen 36 at a pressure sufficient to fill and purge balloon 14 and shaft lumen 36 of unwanted air without also inflating balloon 14. The balloon 14 remains uninflated and wrapped spirally about itself during this step of the inventive purging method. The guide wire director 16, of a permeable plastic material, acts in its entirety as an inlet from lumen 36 to the interior of balloon 14. The lumen outlet 38 is positioned distally of guide wire director 16, allowing for purging of balloon 14. In other preferred embodiments of the inventive method, the guide wire director is non-porous and/or integral with a shaft, and a perforation in the shaft or the director provides a means of fluid communication between the shaft lumen and the balloon interior, thereby defining a lumen inlet proximal to a lumen outlet (e.g., perforation 64 in FIG. 2).

Once the balloon 14 and shaft lumen 36 are filled with inflation medium (and thus purged of air), guide wire 18 is advanced distally through the lumen to form a liquid-tight seal about the guide wire 18 distally of the inlet/guide wire director 16. This liquid-tight seal is demonstrated in FIG. 1, where guide wire 18 is advanced distally of inlet/guide wire director 16 and a liquid-tight seal is formed about guide wire 18 by inflation valve 20 and deflation valve 22.

Preferably, balloon 14 is then filled with inflation medium, after the liquid-tight seal is formed, to place balloon 14 in a fully inflated, unwrapped state. The physician can then ascertain whether the balloon 14 is liquid-tight, has the desired profile, and is ready for use. FIG. 1 shows catheter 10 with balloon 14 in its fully inflated state with a liquid-tight seal formed about guide wire 18. After the inflated balloon has been evaluated, a reverse pressure is applied to inflation lumen 36 from its proximal end. The inflation fluid is thus withdrawn proximally from balloon 14 and balloon 14 returned to its initial spirally wrapped, uninflated state. The inventive purging method attains a sealed, liquid-tight, angioplasty catheter, ready for use on a patient, with a shaft lumen 36 and balloon 14 completely purged of air.

In a preferred use of the inventive method, the guide wire 18 is positioned just proximal of the lumen outlet 38 prior to filling the shaft lumen 36 with inflation medium, as indicated in FIG. 5. With the guide wire 18 positioned in this matter, the liquid-tight seal can be formed rapidly following the filling and purging of the balloon 14 and shaft lumen 36. This step is useful when time is critical during the angioplasty procedure.

The inventive method has been described with reference to the embodiment of a balloon catheter with an inflation-deflation valve seen in FIGS. 1 and 5. It should be recognized that the method is equally applicable to the other illustrated embodiments of the balloon catheter with inflation-deflation valve.

For example, FIG. 2 shows dilatation catheter 50 with the inventive inflation-deflation valve. As seen in FIG. 2, catheter 50 has each of the features necessary to perform the inventive method. An inflatable balloon 54 is provided at a distal end of a shaft 52 which has an inflation lumen 76 extending therethrough. The lumen 76 has at least one inlet (perforation) 64 in communication with the interior of balloon 54 and extends to a lumen outlet 78 distally of the inlet 64. In catheter 50 of FIG. 2, a liquid-tight seal is formed about guide wire 58 following the purging of the balloon 54 and the catheter shaft lumen 76 by inflation-deflation valve components 60 and 62.

FIG. 4A shows dilatation catheter 80, still another embodiment of the balloon catheter with the inventive inflation-deflation valve. As seen in FIG. 4A, catheter 80 also has each of the features necessary to perform the inventive method. An inflatable balloon 86 is provided at a distal of a shaft 84 which has an inflation lumen 106 extending therethrough. In FIG. 4A, as in FIGS. 1 and 5, guide wire director 88 is permeable and acts in its entirety as an inlet providing communication between the lumen 106 and the interior of balloon 86. The lumen 106 extends to a lumen outlet !08 which is distal from the guide wire director 88, as seen in FIG. 4A. A liquid-tight seal is formed about guide wire 82 via inflation of bladder valve 90, after purging.

In summary, the method of the present invention provides for effective purging of a dilatation catheter with an inflation-deflation valve. The purging method does not require separate lumens nor a distal venting device. The inventive method instead provides for purging of a single lumen, over-the-wire catheter by filling the catheter and balloon with inflation medium, thus purging the balloon catheter of unwanted air, and forming a liquid-tight seal about a guide wire distally from an inlet between the catheter shaft lumen and the interior of the balloon. Purging can be accomplished very rapidly by positioning the guide wire just proximal of the lumen outlet prior to purging, providing a significant advantage in a medical procedure where time is a critical factor.

Although the present invention has been described with reference to preferred embodiments, workers skilled in the art will recognize that changes may be made in form and detail without departing from the spirit and scope of the invention.

What is claimed is:

1. A method for preparing an over-the-wire balloon catheter for use prior to the introduction thereof into a patient, wherein the catheter has a shaft with a lumen extending longitudinally therethrough from a proximal end to a distal end, with the lumen having an inlet at the proximal end of the shaft, an outlet at the distal end of the shaft and at least one balloon inflation aperture therebetween, and wherein the catheter has an inflatable balloon about the shaft, with the lumen having its balloon inflation aperture in fluid communication with the interior of the balloon, the method comprising the sequential steps of:

filling the lumen with liquid from the proximal end of the shaft so that liquid is forced out of the lumen through the lumen outlet;

advancing a guide wire distally through the lumen until a distal end of the guide wire is past the balloon inflation aperture of the lumen;

forming a liquid-tight seal about the guide wire in the lumen distally of the balloon inflation aperture; and filling the balloon with liquid after the liquid-tight seal is formed across the lumen to fully inflate the balloon.

2. The method of claim 1, and further comprising the step of:

withdrawing the liquid proximally from the lumen to deflate the balloon.

3. The method of claim 2 wherein the step of forming a liquid-tight seal, during the step of withdrawing the liquid from the lumen, includes creating a net negative pressure within the lumen.

4. The method of claim 1, and further comprising the steps of:

providing the balloon in an initially uninflated state wherein the balloon is wrapped spirally about itself to define a low profile in lateral cross-section; and maintaining the balloon in its wrapped uninflated state until the liquid-tight seal is formed.

5. The method of claim 4, and further comprising the step of:

withdrawing the liquid proximally from the lumen wherein the balloon resumes its spirally-wrapped uninflated state.

6. The method of claim 1, and further comprising the step of:

positioning the distal end of the guide wire just proximal of the lumen outlet prior to filling the lumen with liquid.

7. The method of claim 1 wherein the step of forming a liquid-tight seal includes the step of inflating a bladder within the lumen through a separate bladder inflation lumen extending longitudinally through the catheter.

8. The method of claim 1 wherein the step of forming a liquid-tight seal, during the step of filling the balloon with liquid, includes creating a positive liquid pressure within the lumen.

* * * * *